United States Patent [19]
Bryant et al.

[11] Patent Number: 5,871,926
[45] Date of Patent: Feb. 16, 1999

[54] SENSITIVE METHOD FOR MEASUREMENT OF TELOMERIC DNA CONTENT IN HUMAN TISSUES

[75] Inventors: Jennifer E. Bryant; Kent G. Hutchings, both of Albuquerque, N. Mex.; Robert K. Moyzis, Corona Del Mar, Calif.; Jeffrey K. Griffith, Cedar Crest, N. Mex.

[73] Assignee: The University of New Mexico, Albuquerque, N. Mex.

[21] Appl. No.: 844,642

[22] Filed: Apr. 21, 1997

[51] Int. Cl.$^6$ .................................... G01N 33/574
[52] U.S. Cl. ................ 435/6; 435/7.23; 436/63; 436/64; 436/813
[58] Field of Search .......................... 435/6, 7.23; 436/63, 436/64, 813

[56] References Cited

U.S. PATENT DOCUMENTS

| 5,489,508 | 2/1996 | West et al. . |
| 5,639,613 | 6/1997 | Shay et al. . |
| 5,645,986 | 7/1997 | West et al. . |
| 5,648,215 | 7/1997 | West et al. . |

FOREIGN PATENT DOCUMENTS

93/23572  11/1993  WIPO .

*Primary Examiner*—Toni R. Scheiner
*Attorney, Agent, or Firm*—Hoffman, Wasson & Gitler, P.C.

[57] ABSTRACT

A sensitive method for measurement of telomeric DNA content in human tissue, based upon the ratio of telomeric to centromeric DNA present in the tissue.

6 Claims, 4 Drawing Sheets

SENSITIVE METHOD FOR MEASUREMENT OF TELOMERIC DNA CONTENT IN HUMAN TISSUES

Research leading to the inventions described herein was in part supported by the U.S. Department of Energy and the NIH Minority Biomedical Research Support Program Grant 2-506-GM08139, and the Federal Government has certain rights in this patent.

BACKGROUND OF THE INVENTION

Telomeres, nucleoprotein complexes at the ends of eukaryotic chromosomes, are 10–12 Kbp in length in somatic cells, but as small as 1–2 Kbp in rapidly growing cancer cells. Recent studies have correlated telomere length with the aggressiveness and genetic variability of tumors, making telomere length a potentially informative prognostic factor. Southern blot analysis is currently the standard method for the measurement of telomere length. However, accurate determinations are not possible when DNA is broken or scant, precluding the analysis of many samples, including fixed tissues embedded in paraffin. To avoid these problems, a slot-blot assay that quantitates the relative content, instead of length, of telomere DNA was developed. The relative contents of telomere DNA determined by this slot-blot assay were directly proportional to the relative lengths of telomere DNA determined in parallel by Southern blot analysis in several samples. Relative telomere DNA content could be measured in samples containing as little as 15 ng of total DNA by the slot-blot assay. Relative telomere DNA content, but not length, also was unaffected by breakage of DNA into fragments 1 Kbp or less in length.

DESCRIPTION OF THE DRAWINGS

FIG. 1A Left panel: hybridization with telomere probe. Right panel: hybridization with centromere probe. FIG. 1B Plot of volume integration versus mass of placenta DNA hybridized to telomere specific probe. FIG. 1C Plot of volume integration versus mass of placenta DNA hybridized to centromere specific probe.

SUMMARY OF THE DISCLOSURE

Figure 1A:
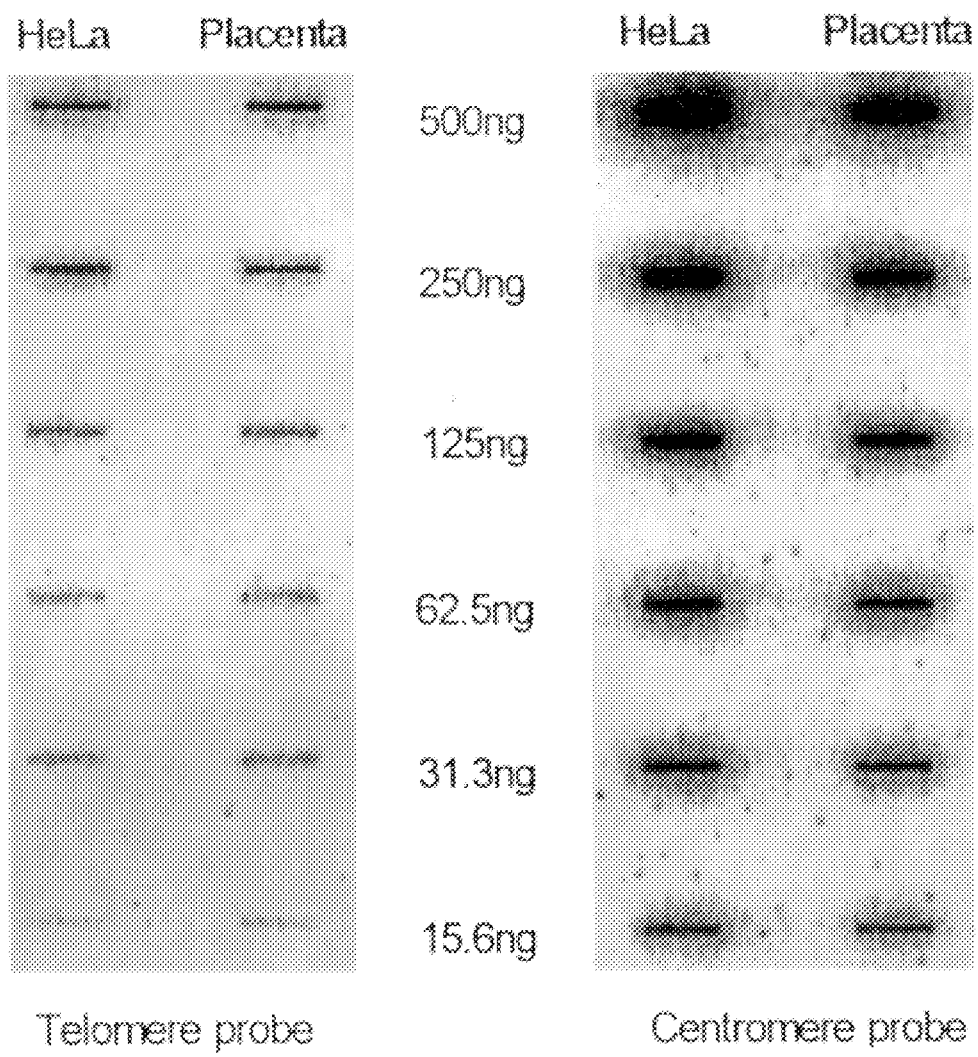
FIGS. 1A–1C. Titration of telomere DNA content by slot-blot.

The invention comprises: 1) a method for indirectly assaying telomere length in a sample of DNA comprising quantitating the sample for telomere DNA content relative to centromere DNA content; and 2) an assay for quantitating relative telomere DNA content in a sample, including the steps of determining telomeric and centromeric DNA content of the sample and calculating the ratio of telomeric DNA to centromeric DNA. In the exemplary slot-blot assay of the invention, telomere content of a DNA sample is quantitated by, for example, hybridizing slot-blotted DNA with telomere- and centromere-specific labelled oligonucleotides, and calculating the ratio of telomeric to centromeric DNA. According to the invention, the relative telomere content of the sample is directly proportional to the relative telomere lengths, and telomere length is therefore readily determined.

The assay is useful for quantitating the relative content of fragmented DNA or very dilute DNA in a sample and obtaining a measurement of relative telomere DNA length, which cannot be accurately done by current standard methods which are based on separation (e.g. gel electrophoresis) of telomeres from other DNA species by size, such as Southern blot analysis.

DETAILED DESCRIPTION OF THE INVENTION

Telomeres, highly conserved nucleoprotein complexes at the ends of eukaryotic chromosomes, consist of tandem repetitive arrays of a TTAGGG motif. Due to incomplete replication of terminal DNA sequences and the absence of telomerase, the ribonucleoprotein that adds telomere DNA to chromosome ends, telomere length is reduced by 40–50 nucleotide pairs with every cell division. Although telomerase is active in cells with extended proliferative capacity, including more than 85% of tumors, telomere lengths in most tumors remain shorter than those in paired normal cells, and ostensibly is related to the number of cell divisions the tumor has undergone.

Several reports have correlated a variety of chromosomal abnormalities, including dicentric chromosome formation, interstitial chromosome translocation, and loss of heterozygosity with telomere length. Since chromosomal abnormalities in tumors are frequently correlated with poor prognosis, their correlation with telomere length could have important implications. Consistent with this view, telomere length in breast cancers has been correlated with aggressiveness of tumors.

Southern blot analysis using a telomere-specific DNA probe is currently the standard method for the measurement of telomere length. Because telomeres are tandem repeats of the single non-palindromic hexanucleotide, TTAGGG, they remain intact after digestion with frequently cutting restriction endonucleases and are subsequently separated by size from other DNA species by gel electrophoresis. However, there are two significant limitations to this method. First, Southern blot analysis of telomere DNA typically requires 1–10 μg of DNA per sample, depending on the length of the telomere. Second, DNA breakage reduces the observed telomere length. These limitations preclude many retrospective and clinical studies, including those utilizing paraffin-embedded, fixed samples in which DNA may be degraded or recovered only in nominal amounts.

The aforementioned problems can be avoided by measuring the content, instead of the length, of telomere DNA. Slot-blot assays are often used as an alternative to Southern blot, northern blot and western blot analyses to detect nucleic acid sequences or proteins in cellular extracts. Because slot-blot assays do not involve separation of DNA by size, they are not affected by DNA breakage or secondary structures. In addition, because the slot-blot assay concentrates the DNA into a single band, instead of the heterogeneous array of restriction fragments produced by electrophoresis, it requires less DNA. In the present study, the sensitivity, specificity, and dependence on DNA integrity of a new slot-blot based assay of telomere content is evaluated.

EXAMPLES

MATERIALS AND METHODS

DNA Isolation. Tissue samples were obtained from the Cooperative Human Tissue network (Columbus, Ohio, USA) and The University of New Mexico Cancer Research and Treatment Center. HeLa cells (ATCC CCL2 HeLa) were obtained and cultured as specified by the American Type Culture Collection (Rockville, Md., USA). Frozen, finely powdered tissue or suspensions of washed cells were mixed with 5 volumes of lysis buffer (0.1M EDTA, 0.5% Sarkosyl, pH 8.0) and 20 μg/ml boiled RNAase at 55° C. in a shaking water bath for 30 min. Proteinase K (United States Biochemical Corp., Cleveland, Ohio, USA) was then added to 200 μg/ml and after 4 hr., the mixture was extracted twice with 2.5 volumes of a 1:1 mixture of phenol and chloroform, and twice with 2.5 volumes of chloroform alone. The solutions containing DNA were then exhaustively dialyzed against TE buffer (1 mM EDTA, 10 mM Tris HCl, pH 7.8), precipitated with ethanol, resuspended in TE, and stored at 4° C.

Preparation of slot-blots. DNA samples (15 ng to 500 ng in 50 μl of deionized water) were diluted with two volumes of 0.5M NaOH, 1.5M NaCl and denatured at 55° C. for 30 min. Prior to completion of the denaturing step, the slot-blot apparatus (Minifold® Slot-blot system, Schleicher & Schuell, Keene, New Hampshire, USA) was assembled according to the manufacturer's instructions using 2 sheets of filter paper layered beneath 1 sheet of Hybond™-N+ paper (Amersham Corp., Arlington Heights, Ill., USA), and the wells were washed twice under vacuum with neutralizing solution (0.5M Tris HCl, 1.5M NaCl). Immediately prior to loading, 500 μl of neutralizing solution was added to each sample. To create the two duplicate blots required for the assay (see below), half of the sample volume was loaded under vacuum onto a well in the upper portion of the slot-blot apparatus and the remaining half was loaded onto a corresponding well in the lower portion. Each well then was washed with 500 μl of neutralizing solution after which the membrane was placed for 20 min. on filter paper saturated with 0.4M NaOH, and rinsed for one min. with 5×SSPE (0.9M NaCl, 0.05M $NaH_2PO_4$, 0.028M NaOH, 0.005M $Na_2EDTA$). The Hybond™-N+ paper was cut in half, creating two replicate membranes, sealed in plastic wrap and stored at 4° C.

Preparation of Southern Blots. Approximately 5 μg of genomic DNA wa digested with restriction endonucleases RsaI and HinfI (New England Biolabs, Boston, Mass., USA), resolved by size in an 0.8% agarose gel and transferred to nylon Hybond™-N+ membrane essentially as recommended by the suppliers. Molecular weight standards (Hind III-digested Lambda phage DNA and "1 Kb" DNA ladders, Life Technologies, Bethesda, Md., USA) were run in parallel.

Preparation of Probes. The telomere specific oligonucleotide $(TTAGGG)_4$ was synthesized by the University of New Mexico Cancer Center Protein Chemistry Laboratory. A centromere-specific oligonucleotide was obtained from Dr. R. K. Moyzis at the Los Alamos Center for Human Genome Studies. The oligonucleotides were end-labeled with 100 μCi γ-$^{32}$P ATP (3,000 Ci/mMol, DuPont NEN, Boston, Mass., USA) at 37° C. for 40 min. using T4 polynucleotide kinase (New England Biolabs, Boston, Mass., USA) with the buffer provided by the supplier. Unincorporated nucleotides were removed by chromatography on Sephadex 50 Nick™ Columns (Pharmacia, Piscataway, N.J., USA) as recommended by the supplier.

Hybridization. The duplicate nylon Hybond™-N+ membranes were incubated in separate 100 ml Bellco Autoblot™ hybridization bottles in 20 mls of a prehybridization solution that contained 5×SSPE, 0.1% sodium dodecyl sulfate, and 20 μg/ml tRNA (Type X, Sigma, St. Louis, Mo., USA) for approximately 2 hr. at 60° C. in a Bellco Autoblot™ hybridization oven (Bellco Glass Company, Vineland, N.J., USA). The specified probes were added and subsequent hybridization was performed at 60° C. in the Bellco Autoblot™ hybridization oven for 16 to 24 hr. The posthybridization washes consisted of two rinses and two subsequent 30 min. washes in the hybridization roller bottle in the oven with 100 ml of 5×SSPE prewarmed to 60° C., and three 7–10 min. washes with 200 ml 0.1×SSPE at room temperature in a flat plastic container on a shaking platform.

Quantification of Telomere Content. Slot and Southern blots were air dried for 30 min. and exposed to a Storage Phosphor Screen (Molecular Dynamics Corp., San Francisco, Calif., USA). The position and density of the telomeric hybridization signals of both the Southern blots and slot-blots were determined with a Molecular Dynamics PhosphorImager™. Time of exposure to the intensifying screen ranged from 4 to 48 hr. Telomere content was determined using the volume integration function of the Molecular Dynamics ImageQuant™ software. A ratio of telomeric DNA content to centromeric DNA content was calculated for each DNA mass (i.e. sample dilution) and then averaged.

Quantification of Telomere Length. Telomere length was determined by comparing the position of the greatest hybridization signal in each lane of the Southern blot to a standard curve derived from the positions of known DNA fragments contained in the "1 Kb" and HindIII-digested lambda phage DNA ladders run in parallel.

RESULTS

Figure 1B:
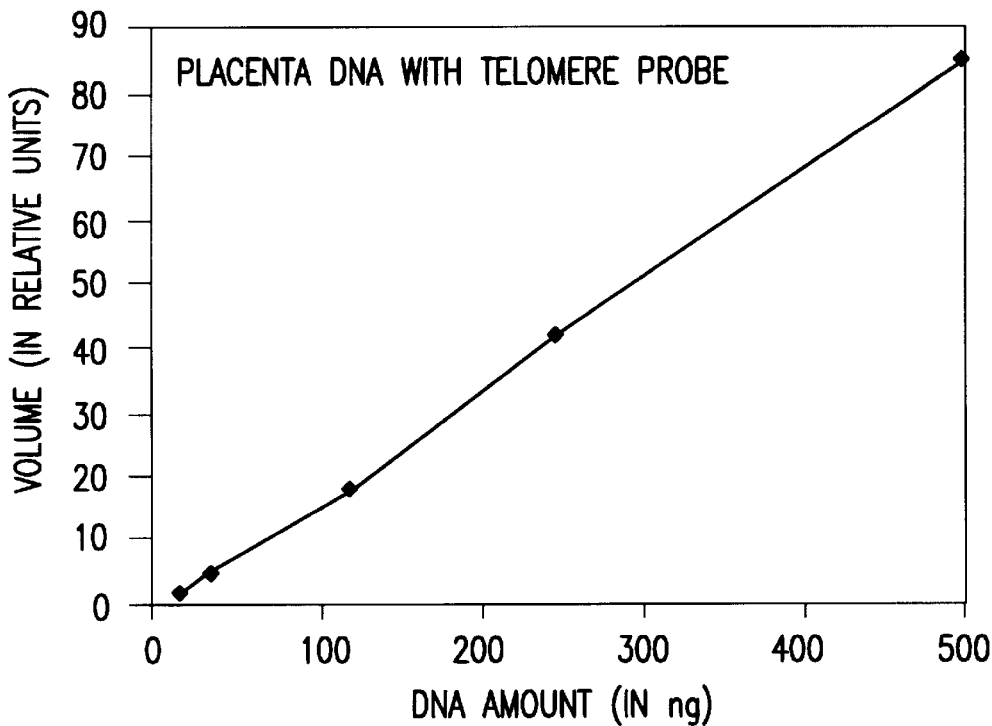
Figure 1C:
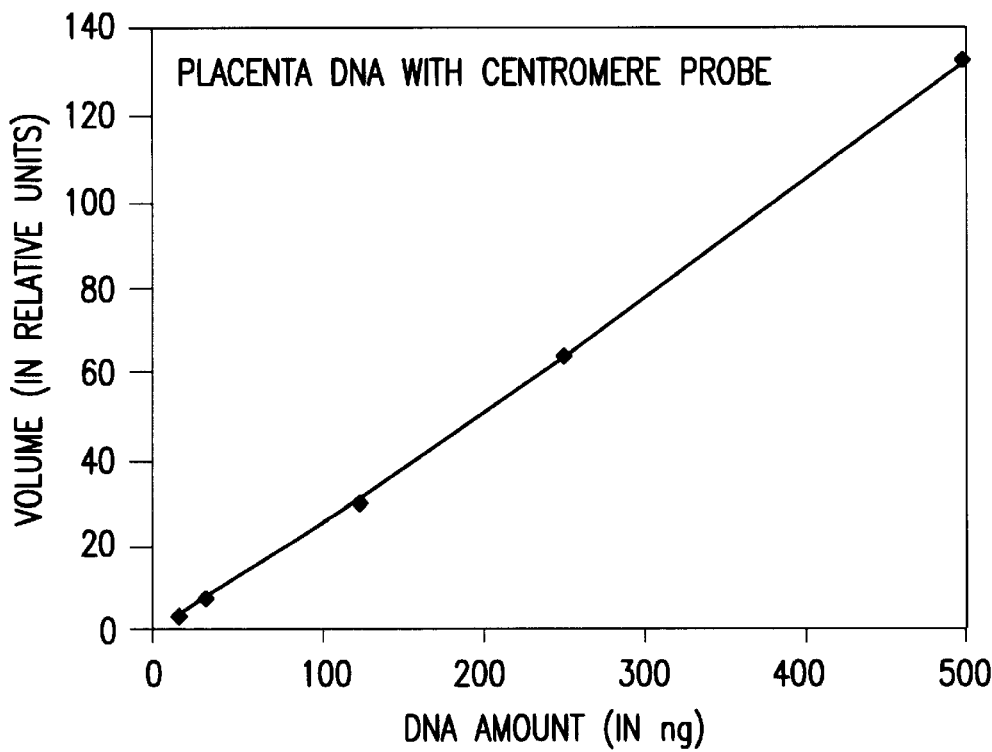

Sensitivity and Specificity. Duplicate blots containing DNA masses of approximately 15 ng to 500 ng of HeLa and placenta DNAs in two-fold increments were hybridized to the telomere-specific and centromere-specific oligonucleotides. When analyzed by Phosphorimager™, the intensities of the hybridization signals were directly proportional to the mass of DNA in each "slot" over the entire range of DNA masses tested (FIG. 1). In contrast, neither the telomere- nor centromere-specific probes produced detectable signals with 1 μg of DNA from the bacterium Micrococcus Iuteus (not shown), verifying the specificity of hybridization with the telomere and centromere probes.

Telomere Content in HeLa and Placenta DNA. Southern blot analysis demonstrated that the mean telomere length in HeLa DNA, a model for immortalized cells, was 53.1% (SD±8.1%) of the length in placenta DNA, a model for somatic cells. Virtually identical results were obtained with the slot-blot assay. Three serial dilutions of HeLa and placenta DNA were analyzed for each set of slot-blot. The ratio of "telomere probe signal intensity" to "centromere probe signal intensity" (T/C ratio) was used to normalize for variability in DNA content. The T/C ratio for the HeLa DNA was 51.9% (SD±3.5%, n=11) of the T/C ratio for the placenta DNA.

Figure 2:
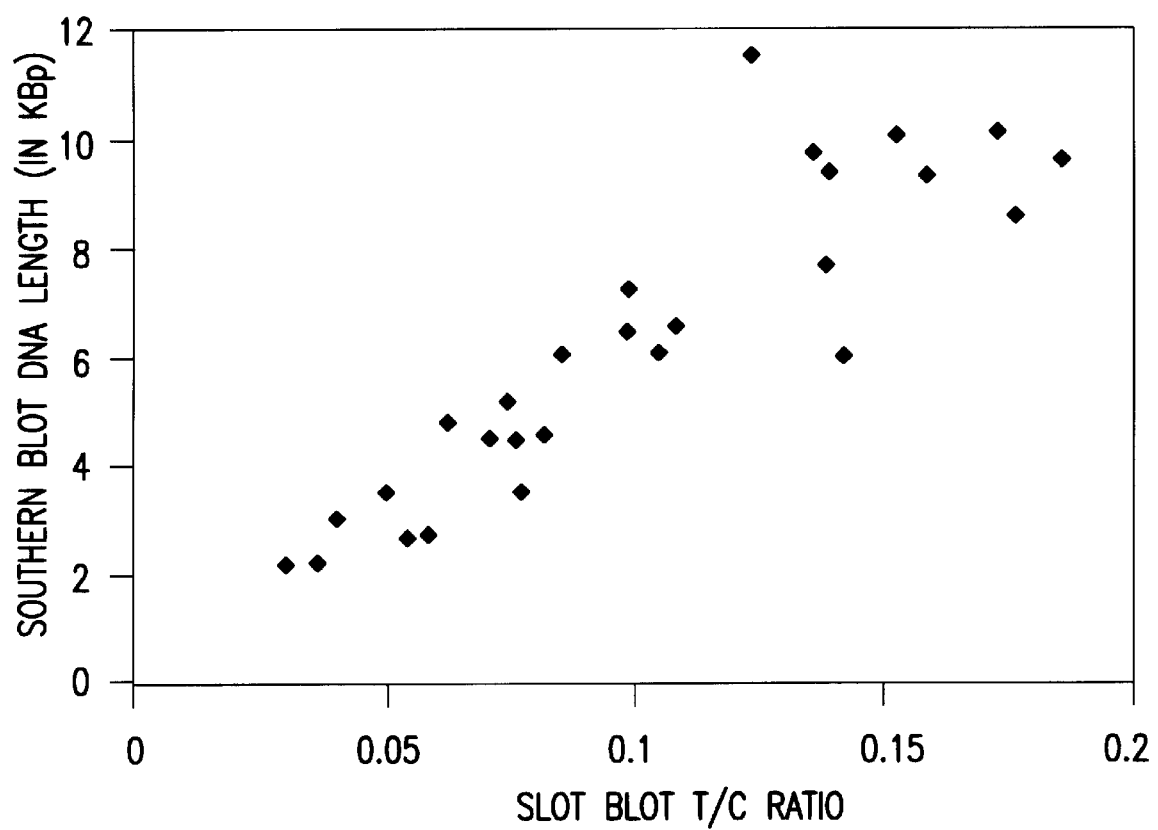
FIG. 2. Length versus content of telomere DNA. Relative telomere contents (T/C ratios) and lengths were measured in 28 DNA samples by slot-blot and Southern blot assays, respectively.

Telomere content in DNA from Human Tissue Samples. Relative telomere content, defined by the slot-blot assay, was compared to relative telomere length, defined by Southern blot analysis. T/C ratios were calculated for 28 independent DNA samples isolated from cancerous and normal human tissue. Two and three dilutions of each sample were analyzed in order to confirm linearity between dilutions, and to ensure that the hybridization signal for each sample would fall within the standard curve of the HeLa and placenta control samples. Although the absolute value of the T/C ratio differed between independent experiments due to variation in the probes' specific activities, the constant relationship between the ratios of HeLa and placenta DNA that are run as controls on every blot allowed for relative DNA contents to be compared. The mean telomere length also was determined for each of the 28 samples by Southern blotting. As shown in FIG. 2, the relative content of telomere DNA was directly proportional to telomere length (r=0.904).

Figure 3:
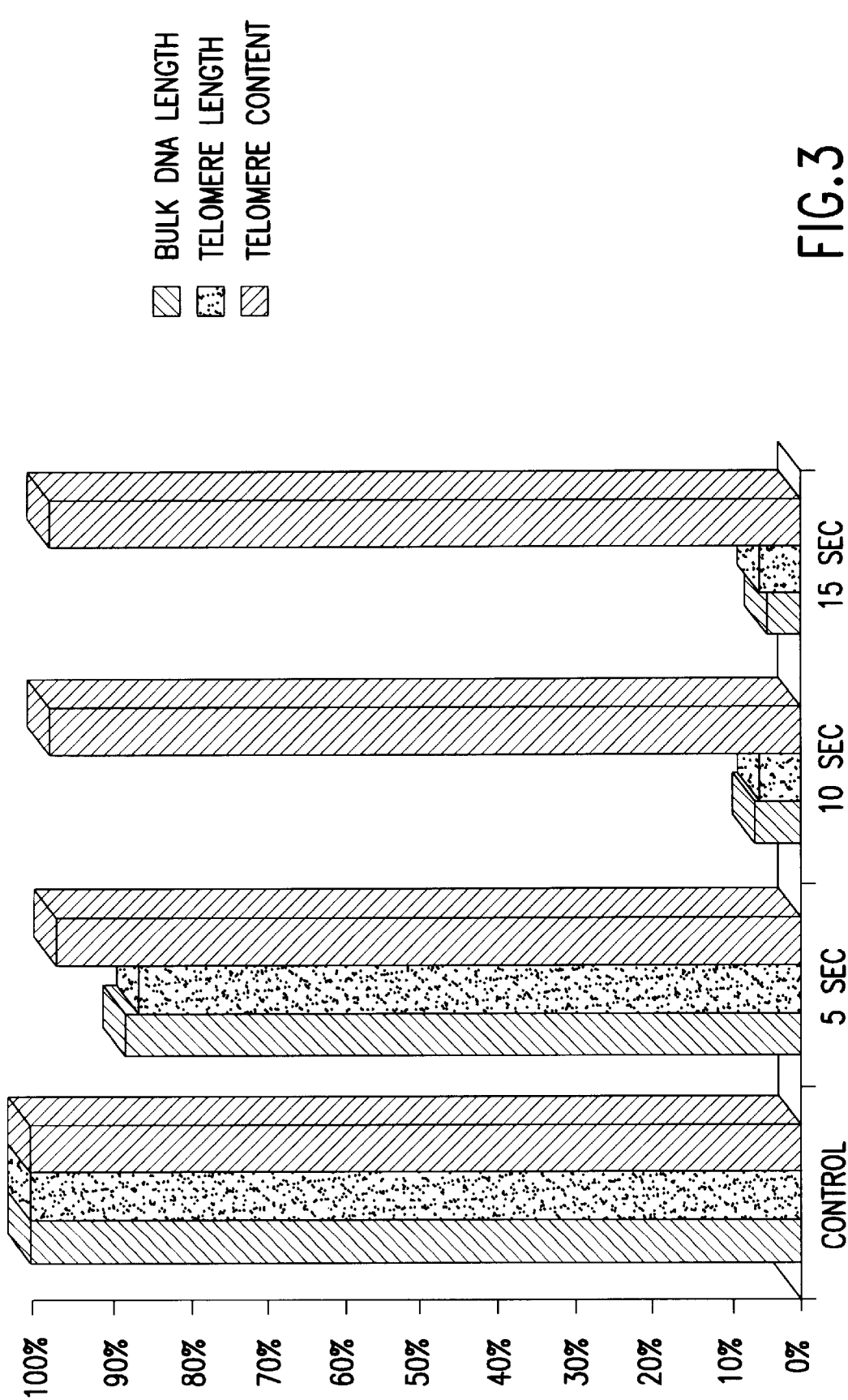
FIG. 3. Effects of DNA breakage on telomere length and content. Relative telomere contents (T/C ratios) and lengths were measured in sonicated DNA samples by slot-blot and Southern blot assays, respectively. Data is expressed as the percent of the bulk DNA fragment size, telomere content and telomere length measured in unsonicated DNA assayed in parallel.

Effect of DNA Breakage. Because the slot-blot assay does not involve the separation of DNA by size, telomere breakage would not be expected to affect measurement of the content of telomere DNA. To test this prediction, DNA extracted from placenta cells was sonicated for 1, 5, 10 and 15 sec. (FIG. 3). Placenta DNA sonicated for 1 sec. was greater than 12 Kbp in length when compared to a 1 Kbp ladder run in parallel. DNA sonicated for 5 sec. was noticeably smaller than the 1 sec. control, but the largest fragments still exceeded 12 Kbp. After the DNA had been sonicated for 10 sec., a heterogeneous range of DNA fragments overlapped the 1 Kbp size marker. Sonication for 15 sec. produced a heterogeneous range of smaller DNA fragments between 0.5 and 1 Kbp. Paired aliquots of DNA then were analyzed using slot-blot and Southern blot assays. When analyzed by Southern blot, there was a progressive shortening of telomere size that mirrored the extend of fragmentation of the bulk DNA. In contrast, the content of telomeric DNA, as defined by the slot-blot, was almost identical for each sample regardless of fragment length.

An assay for measuring the relative content of telomere DNA in normal and tumor cells demonstrated that telomere content, as defined by this assay, is directly proportional to telomere length, defined by Southern blot analysis. The slot-blot is easily quantitated and, unlike Southern blot analysis, can be performed with as little as 15 ng of DNA and is not affected by DNA breakage. This is particularly advantageous for retrospective or clinical studies utilizing paraffin-embedded, fixed samples from which DNA is recovered in small amounts and is subject to breakage. In this context, preliminary studies indicate that telomere content in DNA extracted from paraffin embedded, fixed tissue is similar to that in DNA extracted from fresh or frozen tissue. Thus, the invention provides a valuable tool for assessing the relationship between telomere content and prognosis since it makes possible retrospective studies of archival material obtained from cancer patients whose complete histories and outcomes are known. If contamination by normal cells is reduced by microdissection, analysis of nearly pure tumor cell populations is therefore feasible. Owing to the much greater sensitivity of the slot-blot assay, and its insensitivity to DNA breakage, analysis can be performed on DNA purified from sectional tissue which has been characterized microscopically.

We claim:

1. An assay for determining telomere length in a sample of DNA comprising quantitating telomere and centromere content of the sample, and calculating the ratio of telomeric to centromeric DNA present.

2. The assay of claim 1, wherein the assay is a slot-blot assay.

3. The assay of claim 2, wherein slot-blotted DNA is hybridized with telomere- and centromere-specific oligonucleotide probes for assay.

4. The assay of claim 1, wherein the DNA is obtained from paraffin-fixed tissue.

5. A method for the evaluation of the metastatic potential of a tumor, comprising assaying the tumor cells for telomeric length according to the assay of claim 1.

6. The method of claim 5, wherein the tumor is a breast or prostate tumor.

* * * * *